United States Patent [19]

Lübbers et al.

[11] Patent Number: 4,511,660
[45] Date of Patent: Apr. 16, 1985

[54] PROCESS AND ARRANGEMENT FOR MEASURING ION STRENGTH

[76] Inventors: Dietrich W. Lübbers, Rheinlanddam 201a, D-4600 Dortmund; Norbert Opitz, Marianstrasse 18, D-4630 Bochum, both of Fed. Rep. of Germany

[21] Appl. No.: 503,251

[22] Filed: Jun. 10, 1983

[30] Foreign Application Priority Data

Jun. 14, 1982 [DE] Fed. Rep. of Germany ....... 3222325

[51] Int. Cl.$^3$ ..................... G01N 21/00; G01N 21/77; G01N 27/36
[52] U.S. Cl. .................................. 436/163; 204/420; 204/433; 324/438; 436/172
[58] Field of Search ........................ 204/1 H, 1 T, 420, 204/433; 324/438; 422/52; 436/163, 172

[56] References Cited

U.S. PATENT DOCUMENTS 3,894,917 7/1975 Riseman et al. ............... 204/419 X
4,002,428 1/1977 Blanchard ....................... 324/438 X
4,028,196 6/1977 Young ............................. 204/1 T

FOREIGN PATENT DOCUMENTS 2159096 5/1973 Fed. Rep. of Germany ...... 324/438
2548518 5/1977 Fed. Rep. of Germany ...... 324/438

OTHER PUBLICATIONS

Britton, "Hydrogen Ions" 3rd Edition, Vol. 1 pp. 375–382 (1943).
A. Scarpa, Kinetic and Thermodynamic Aspects of Mitochondrial Calcium Transport, 1976, pp. 31–45, Academic Press.
S. Udenfriend, Fluorescence Assay in Biology and Medicine, Appendix I, Table I, 1962, p. 472, Academic Press.

Primary Examiner—Arnold Turk
Assistant Examiner—Robert Hill
Attorney, Agent, or Firm—Cushman, Darby & Cushman

[57] ABSTRACT

Process and apparatus for directly measuring the ion strength of an electrolyte solution is disclosed. The pH value of the electrolyte is measured by means of a first measurement with a first indicator dependent on the ion strength and by means of a second measurement with a second indicator dependent on ion strength in a manner different from the first indicator whereby the ion strength is computed by means of the approximation $$J = J_o \times 10^{F(N)} \left[ 1 + \frac{W(X) + 0.5}{W(N) - W(X)} \right] [pH'(N) - pH'(X)] \quad (2)$$

J = ion strength
Jo = ion strength upon calibration
pH'(N) = pH value, measured with a first indicator N dependent on the ion strength (HPTS)
pH'(X) = pH value, measured with a second indicator X dependent on the ion strength, the ion strength dependence of which is different from that of the first indicator
W(N) = valency of the first indicator
W(X) = valency of the second indicator
with $$F(N) = -\frac{1}{0.07[ZW(N) + 1]}. \quad (2a)$$

The ion strengths of other ions and of unknown electrolyte may also be computed.

18 Claims, 4 Drawing Figures

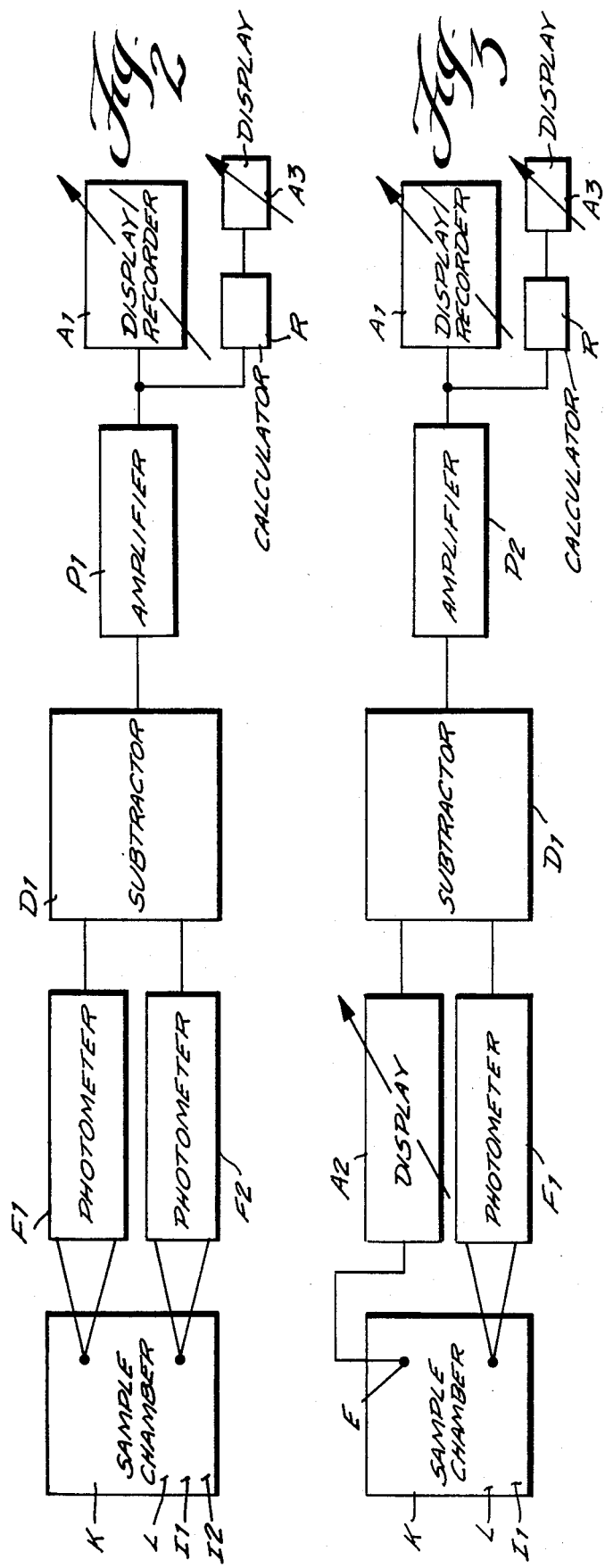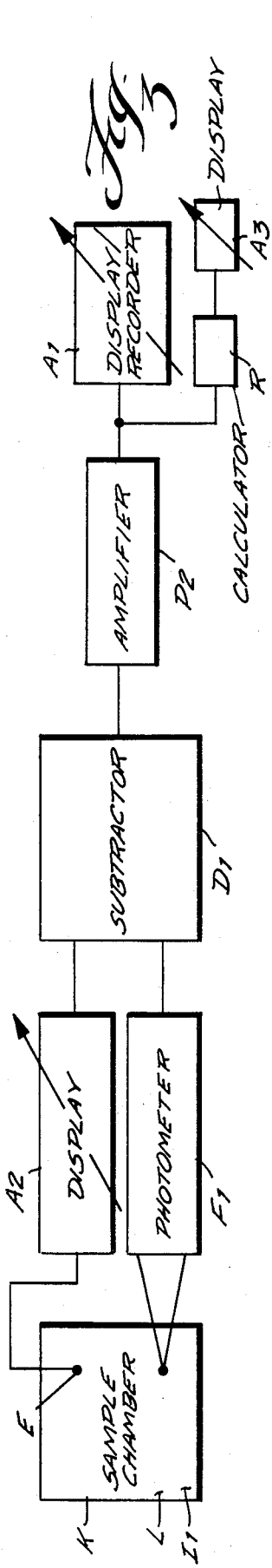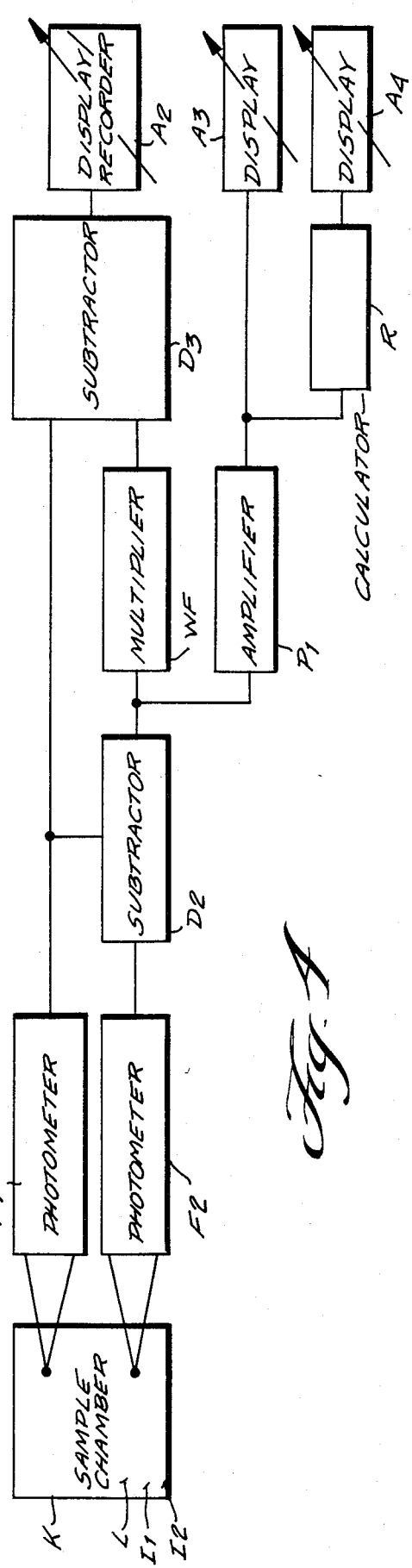

PROCESS AND ARRANGEMENT FOR MEASURING ION STRENGTH

BACKGROUND OF THE INVENTION

This invention concerns a process and an arrangement for measuring ion strength.

The ion strength J of an electrolyte is defined by $$J = \frac{1}{2} \sum_i C_i W_i^2 \qquad (1)$$

wherein in the definition Ci stands for the concentration of the species i and Wi stands for valency of the species i. Whenever ion strength is to be determined, the concentration of the individual species must accordingly be measured and the ion strength according to equation (1) is calculated from the electrochemical valencies of the particular ion species as customarily determined from published tables of such data.

For most routine measuring and interpretation problems, such a determination of the ion strength is sufficient. In the case of biological objects however, for example in the case of metabolism processes, frequently temporal changes of the composition of the substance occur in the electrolytes. Consequently in such cases if the pertinent ion strengths are to be determined, it is cumbersome to determined the fractions of the participating substances as well as their valencies and concentration and then do calculations by way of the tables. Such a procedure is in most cases not possible in the short processing time which is available.

OBJECTS AND SUMMARY OF THE INVENTION

The invention provides a more efficient process and arrangement for the immediate measurement of the ion strength of electolytes.

The invention solves this task through the fact that the pH value of the electrolyte is measured with a first indicator dependent on the ion strength and a second indicator depending in a different manner from the first indicator on the ion strength, whereby the ion strength is calculated by means of the formula $$J = J_o \times 10^{F(N)} \left[ 1 + \frac{W(X) + 0.5}{W(N) - W(X)} \right] [pH'(N) - pH'(X)] \qquad (2)$$

J = ion strength
Jo = ion strength upon calibration
pH' (N) = pH value, measured with a first indicator N dependent on the ion strength (HPTS)
pH' (X) = pH value, measured with a second indicator X dependent on the ion strength, the ion strength dependence of which is different from that of the first indicator
W(X) = valency of the first indicator
W(N) = valency of the second indicator
with $$F(N) = \frac{1}{0.07 \, (2W(N) + 1)} \qquad (2a)$$

The advantage of the process of the invention lies in the fact that now the ion strength is determinable directly even from mixtures of a per se unknown compound.

It is another object of the present process to provide a means for safely determining the pH of electrolyte solutions in locations having a risk of explosion.

A still further object of the present invention is to provide a safe and efficient diagnostic apparatus and process.

Other objects and advantages of the present invention invention will appear from the following detailed description taken in conjunction with the drawings.

BRIEF DESCRIPTION OF THE DRAWINGS

FIGS. 2, 3 and 4 schematically illustrate three simple different arrangements for conducting the present process.

DETAILED DESCRIPTION OF THE INVENTION

Figure 1:
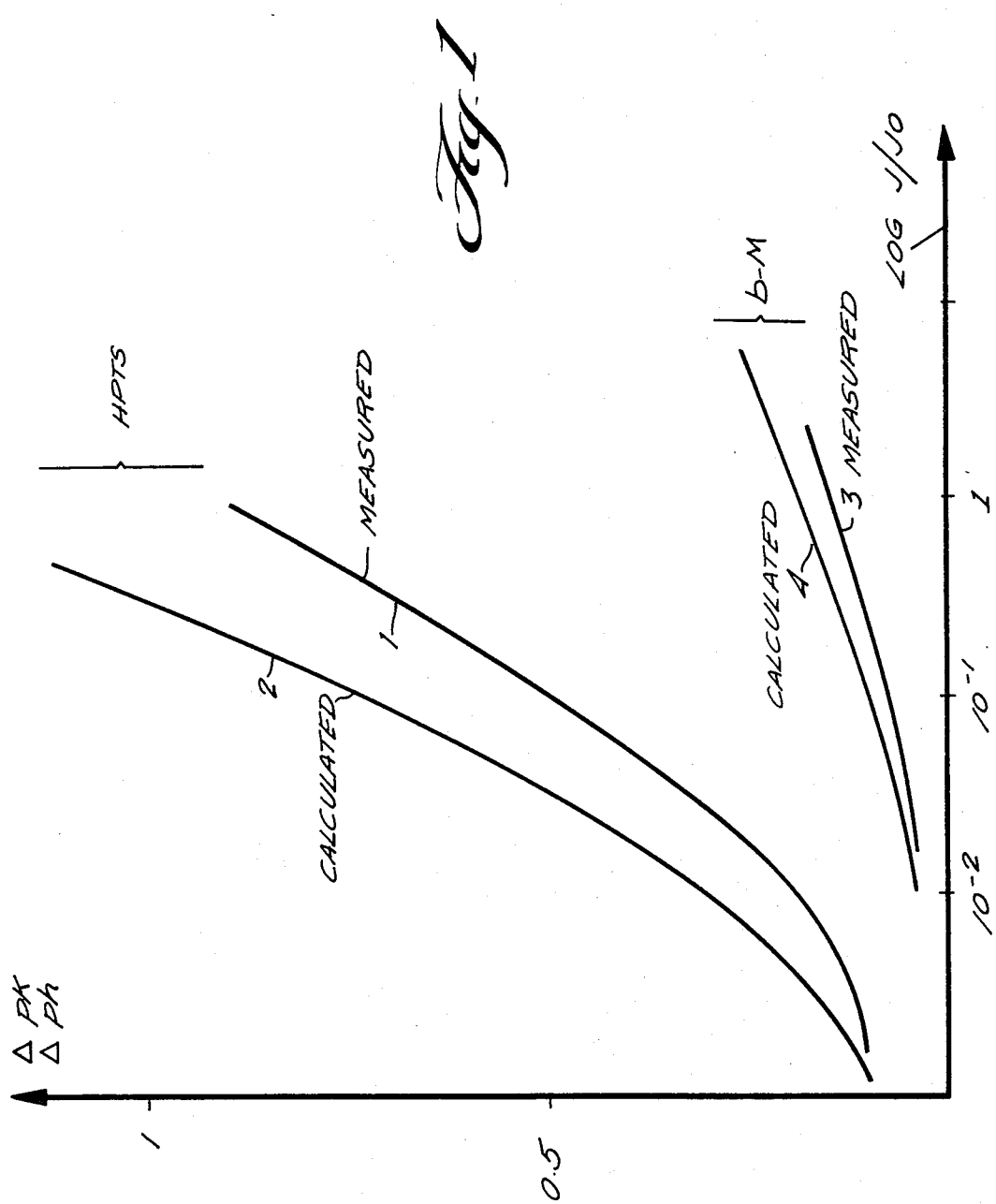
FIG. 1 shows comparison curves between curves plotted from measured values and theoretical values for hydroxypyrentrisolfonate (HPTS) and b-methylumbelliferon (b-M).

An arrangement for carrying out the process employs various integrally interacting components. The pH value may be determined by means of a first indicator dependent on the ion strength, and also by a second indicator with a different dependence on the ion strength as compared to the first indicator. The difference of the two pH values is used as an exponential power for raising a portion of the quantity in formula (2) to that power, i.e. by raising signal $E_1$:

$$E_1 = J_o \times 10^{F(N)} \left[ 1 + \frac{W(X) + 0.5}{W(N) - W(X)} \right] \qquad (3)$$

The raised signal is fed to an indicating device for recording or displaying, for example, the ion strength of the electrolyte.

The process may be carried out with fluorescence indicators, absorption indicators, electrode indicators or any other recording processes. However, the two measurements must have a different dependence on the ion strength. The electrodes may be glass electrodes or ion selective electrodes, for example, for the pH measurement, ion selective or glass electrodes for the measurement of Ca-ions. For example in the fluorescence photometric measurement of calcium ions, one may use Arsenazo-III as an absorption indicator. Arsenazo-III is described in Scarpa, Kinetic and Thermodynamic Aspects of Mitochondrial Calcium Transport, Acamedic Press, pp. 31–45 (1976), the disclosure of which is herein incorporated by reference. In particular, Arsenazo III, (2,2'-(1,8-dihydroxy-3,6-bisulfo-2,7, naphthalenebis (azo) dibenzene, is a very sensitive calcium ion indicator. Each indicator, of course, undergoes a color change generally characteristic of the indicator which can be correlated against the concentration of the ions in the sample.

A special process for simultaneous measurements is the double indicator process, namely the measurement with two different fluorescence indicators, because their fluorescence signals are easily separated in measuring techniques. For physiological measurements, especially of blood and urine, the use of hydroxypyrenetrisulfonate (HPTS) and b-methylumbelliferon (b-M) are particularly advantageous. HPTS and b-M are described herein as exemplary indicators. Furthermore, a reference indicator may be assigned to the fluorescence indicator in order to eliminate intensity fluctuations in a known manner.

In the event that the pH value is to be determined by means of (i) of fluorescence photometric measurement and (ii) a pH measurement with a pH glass electrode as an indicator, the ion strength will be calculated by means of the formula:

$$J = J_o \times 10^{2.22 \, [pH'(N) - pH]} \quad (4)$$

pH' (N) = pH value measured with a first indicator N (HPTS)

pH = pH value measured with a pH electrode.

Apparatus for carrying out this process is composed of, for example, an arrangement for first measuring the pH by fluorescence photometric means and a pH electrode for the second measurement of the pH value, and means for determining the signal difference between the two pH measurements. The signal difference between the first and second pH measurements is used as an exponent of a product $E_2$ wherein:

$$E_2 = J_o \times 10^{2.22} \quad (5) \text{ ps}$$

Then $E_2$ as raised by the difference signal exponential power is fed to using means such as an indicator, display, and/or calculating device.

A description of a suitable first fluorescence photometric measurement means for the pH value determination is described in applicant's own prior U.S. Pat. No. 4,003,707 (1977), the disclosure of which is incorporated herein by reference. In FIG. 2, F1 and F2 are spectrometers in accordance with said U.S. patent for measuring an electrolyte solution in a common non-flow-through chamber. D1 is a substracting network. P1 is an amplifier elevating output of D1 to a power as, for example, in accordance with equation 3. The signal from P1 is then displayed as a value on instrument A1 or after further refinement and computation on instrument A3.

Referring now to such an arrangement for the fluorescence measurements, a test solution of known ionic strength is placed in the sample chamber in the fluorescence photometric measuring arrangement. Next, a fluorescence pH indicator, such as 4-methylumbelliferon, is added to the known test solution in the sample chamber and the fluorescence then measured. Subsequently, a conventional glass electrode is used to measure the pH of the test solution. This provides for the value of $J_o$ which is the known value of the ionic strength of the test solution, assuming, of course, that the same instrument and electrode are subsequently employed for measuring ion strengths. Thus, using $J_o$ as the reference point on the scale, the actual "J" value is determined in accordance with formula (4) of which formula (2) is a generalization, but $J_o$ is similarly determined in any case.

Each of the measuring means is selected so that the signal difference between the output signals of each of the measuring means will have the greatest possible value. This will minimize any percent errors in the final determinations of pH, osmolarity or the like. In this respect, the use of pH electrodes or of selective electrodes is of advantage, because the electrodes have only a slight dependence on the ion strength. Consequently, the signal difference between the measuring means is particularly great, and since the signal difference is used as an exponential power the resulting measurement signal, too, is particularly great. This advantage will be even further enhanced through the fact that the valency of the used first indicator is preferably as high as possible.

In the case of the described measuring methods and arrangement, using HPTS as a fluorescence indicator for the pH measuring is arbitrary. Other fluorescence indicators are also suitable and are described in, for example, Undenfriend, Fluorescence Assay in Biology and Medicine, Appendix I, Table I, page 472, Academic Press (1962), the disclosure of which is hereby incorporated by reference. The exponent factor for the indicator HPTS is about 2.22. However, in the event another fluorescence indicator is used, the exponent factor is different and can be determined as follows.

The exponent factor F(X) assigned to any given indicator (X) may be determined without any trouble in accordance with the formula:

$$F(X) = F(N) \frac{Z(N)}{Z(X)} \quad (6)$$

wherein

F(N) represents the indicator specific exponent constant for N (HPTS),

F(X) represents the exponent constant for indicator X,

Z(N) represents the valency parameter for N (HPTS), and

Z(X) represents the valency parameter for indicator X and wherein $$Z = 2(-W) - 1 \quad (7)$$

W being the valency.

Consequently while one embodiment of the invention is described in terms of HPTS and b-M, it should accordingly be understood that other fluorescence indicators may be substituted therefore following adjustment of the exponent factor F(X). With arrangements of this kind and by recalculation, the osmotic pressure and the increase of the boiling point are readily determined. For instance, the osmotic pressure $P_o$ is:

$$P_o \cong 2|J| \times 22.4 \text{ atm} \quad (8)$$

and for the osmolarity, it is:

$$O_{sm} \cong 2J. \quad (9)$$

The process of the present invention may also be used for fluorescence photometrically determining the pH value of a solution with unknown ion strength or of unknown solutions of electrolytes.

Whenever a fluorescent pH indicator photometerizes, it turns out that the measured pH value deviates from the actual pH value. The deviation is dependent on the ion strength of the elctrolyte being measured. To eliminate this deviation, the pH value is measured with two different indicators having a variable or different dependence on the ion strength, and the actual pH value is determined by means of the formula:

$$pH = pH'(X) - \frac{W(X) + 0.5}{W(N) - W(X)} [pH'(N) - pH'(X)] \quad (10)$$

wherein
- pH′ (N) represents the apparent pH(N) value,
- pH′ (X) represents the apparent pH(X) value,
- pH represents the actual pH value,
- W(X) represents the valency for indicator X, and
- W(N) represents valency for indicator N.

Such an optical method of the pH measurement may be used advantageously, for example, for process control, because it can be accomplished on a continuous basis.

Furthermore, it will be possible to use the present measurement method in places or locations endangered by explosion, since the present process may be accomplished, for example, by way of light conductors. Consequently, all electric potentials such as, for example, the supply voltages of the measuring arrangement, may be avoided in such a place or location.

The measuring method will now be explained as follows and for brevity mathematical formulas are provided. It should be understood that the formulae and equations are recited herein for the purpose of explanation.

Starting point is the mass action law in the form:

$$pH = pK - \text{Log}\left(\frac{Sd - Sx}{Sx}\right) = pK - \text{Log}(1-\alpha)/\alpha \tag{11}$$

with
- Sd = concentration of the completely dissociated electrolyte
- Sx = concentration of the actually dissociated part of the electrolyte
- $\alpha$ = Sx/Sd = degree of dissociation of the electrolyte As determined experimentally, the pH shift of the fluorescence photometrically measured pH value is proportional to:

$$\Delta pk = pk_1 - pk_2, \tag{12}$$

wherein:
- pk1 = pk-value at ion strength 1
- pK2 = pk-value at ion strength 2.

Hence, in the case of two measurements of the same solution with different pH indicators each having variable dependence of the ion strength, there results the formula system:

$$pH = pH'(N) - \Delta pk(N)$$

$$pH = pH'(X) - \Delta pk(X). \tag{13}$$

In those two equations (13), the values of pH, $\Delta pK(N)$, $\Delta pK(X)$ are unknown. Hence, while seemingly unsolvable, equations (13) may however be solved, when one considers that according to the DEBYE-HUECKEL theory there exists an approximation and coupling of the deviations $$\Delta pK(N), \Delta pK(X)$$

According to the DEBYE-HUECKEL theory, $$pK = (Z) \times L(J) \tag{14}$$

wherein $$Z = 2(-W) - 1 \tag{15}$$

and W = valency of the indicator.

According to the DEBYE-HUECKEL function:

$$L(J) = A \frac{\sqrt{J}}{1 + Bd\sqrt{J}} \tag{16}$$

wherein in equation (16) J represents the ion strength, Bd represents the molecular parameter, and A represents a temperature dependent constant. Thus, starting from equation (13) and employing the approximation:

$$L(J,X) = L(J,N) \cong L(J) \tag{17}$$

the following formulas result:

$$\Delta pk(N) = Z(N) \times [L(J)]$$

$$\Delta pk(X) = Z(X) \times [L(J)]. \tag{18}$$

Therefore, the following coupling exists in accordance with:

$$\Delta pK(N) = \frac{Z(N)}{Z(X)} \cdot (\Delta pK(X)). \tag{19}$$

From equations (13) and (19), there follows:

$$pH = \frac{1}{Z(X) - Z(N)}[Z(X)pH'(N) - Z(N)pH'(X)] \tag{20}$$

or with the valencies W:

$$pH = pH'(X) - WF[pH'(N) - pH'(X)] \tag{21} \text{ ps}$$

with $$WF = \frac{W(X) + 0.5}{W(N) - W(X)}.$$

Experimentally, the following curves result for HPTS and b-M as shown in FIG. 1:

For HPTS, there is obtained, for example:

$$\Delta pK (HPTS) = 0.45 \text{ Log} \frac{J}{J_o} \tag{22}$$

and for b-methylumbelliferon (b-M), for example, there is obtained:

$$\Delta pK (b-M) = 0.07 \text{ Log} \frac{J}{J_o} \tag{23}$$

in the practically most important ion strength range $$J_o < J < 10 J_o; J_1 = 0.1$$

which are shown in FIG. 1.

Curve 1 is the measured curve for HPTS, curve 2 the curve to be expected according to the DEBYE-HUECKEL theory for HPTS, curve 3 is the measured curve for b-M and curve 4 is the curve for b-M to be expected theoretically according to the DEBYE-HUECKEL theory.

Recalculated, there results from the formulas (22), (23) the ion strength in the case of the measurement of the pH values by a pH electrode and by means of fluorescence photometry (indicator HPTS):

$$J = J_o \times 10^{1/.045[(pH'(N)-pH)]} = J_o 10^{2.22 \, (pH'(N)-pH)} \tag{24}$$

and in the case of measurement with two fluorescence indicators, say HPTS and b-methylumbelliferon, at:

$$J = J_o \times 10^{2.22} (1 + WF)(pH'(HPTS) - pH'(b\text{-}M)) \quad (25)$$

with WF being determined in accordance with 21(a):

$$WF = \frac{W(X) + 0.5}{W(N) - W(X)} = \frac{W(b - M) + 0.5}{W(HPTS) - W(b - M)} =$$

$$\frac{-1 + 0.5}{-4 + 1} = \frac{1}{6}$$

Similarly, for any indicators X, the following is valid:

$$J = \qquad (26)$$

$$J_o \times 10^{F(N)} \left[ 1 + \frac{W(X) + 0.5}{W(HPTS) - W(X)} \right] [pH'(HPTS) - pH'(X)]$$

with $$F(N) = \frac{1}{0.07 \, (Z(N))} \quad (26a)$$

and $$Z(N) 2(-W(N)) - 1 \quad (26b)$$

At the same time, F(N) may be found as follows. The formula (24) corresponds to the formula (2). The factor F=2.22 in formula (24) is therefore approximately the inverse value of the rise of 0.45 of the curve (22). The rise will be effectively determined experimentally, but in principle the rise may also be determined theoretically according to the DEBYE-HUECKEL theory.

At the same time standardization is arbitrary and one may also standardize to any other indicator.

In principle, the formula is valid for any ions, since characteristics of a certain ion type do not have to be presupposed. The two indicators required for the measurement of a certain type of ion however must depend in a variable, i.e., different, manner on the ion strength of the solution.

FIGS. 2 and 3 show simple arrangements with which the described method may be carried out.

In FIG. 2, two fluorescence photometers F1, F2 adjusted to the pH sensitive indicators I1, I2, determine the pH value of the same solution L in common sample chamber K. The common sample chamber may, for example, be a closed bulb, but in any event it should not be a flow-through chamber. F1 and F2 may each be like the photometer or spectrometer described in applicants' own U.S. Pat. No. 4,003,707, e.g., FIG. 1, but they share a single chamber and are regulated to depend their outputs differently on the ion strength. The two respective pH value signals from F1 and F2 are fed electrically to a subtractor D1 which operates on the pH signals from F1 and F2 and produces a difference signal. Already set into amplifier P1 is a signal E, which is determined as follows:

$$E_1 = J_o \times 10^{F(N)} \left[ 1 + \frac{W(X) + 0.5}{W(N) - W(X)} \right] \quad (3)$$

All of the values needed to make up the $E_1$ signal are known and preset into amplifier P1 which develops the $E_1$ signal and this $E_1$ signal is then raised in amplifier P1 by an exponential power corresponding to the difference of the two pH signals:

$$pH'(N) - pH'(X). \quad (3a)$$

The value J formed in the amplifier P1, which may be developed as an operational amplifier or as a digital counter, is recorded in and/or displayed by instrument A1.

In conjunction with the ion strength indication, a recalculation of the signal may take place in a calculating device, i.e., calculator, R, so that in an indicating or displaying apparatus A3, additional deducible, i.e. derived, signals corresponding to further characteristics of the electrolyte solution may be simultaneously displayed. For example, if a multiplication with 2 takes place in R, then the indicating apparatus shows the osmolarity according to equation (9), but if the factor is of the magnitude 44.8, then A3 indicates the osmotic pressure according to equation (8).

It will be appreciated that if necessary the work of D1, P1 and R may be done on line with a computer.

Other counting rules which depend on the ion strength may also be used.

In FIG. 3, the electrode E has replaced the photometer F2 and the indicator I2 in sample chamber K containing sample solution L. In such an arrangement, it is easy to indicate the pH value additionally by an indicating display arrangement A2. Thus, for example, in the case of metabolism processes, the reference to changes of one composition of the substance is made possible, which may result in the case of a constant pH value and which is of significance diagnostically. The measurement of deduced values is accomplished by the FIG. 2 apparatus in keeping with above equations (4) and (5) by using the signal difference between E and F1 determined by subtractor D1 as an exponential power by which a product signal such as $E_2$ in equation (5) is raised in amplifier P2. The amplifier signal is then fed to display recorder A1 and/or calculator R for an operation as in equation (8) or (9) before being displayed with instrument A3.

In FIG. 4, the pH value of the sample L in the sample chamber K, for example a bulb, is measured with the two photometers F1 and F2, and the signal difference is formed in the subtracting member D2. After multiplication with the valency factor by multiplier WF (equation 21a), this signal is once more subtracted in subtractor D3 from the signal of the indicator I1 and is recorded by the recording arrangement A2. Thus the WF (multiplier), D3, A2 branch of the arrangement depicted in FIG. 4 is designed to produce a display of the true pH, i.e., the pH after correcting for the influence of the ionic strength in keeping with equation (10) or (21).

The parallel measurement of the ion strength is accomplished in FIG. 4 through the fact that the differential signal from subtractor D2 is also fed to amplifier member P1 which operates as in FIG. 2 to raise the basic preset signal $E_1$ to the power represented by the signal difference from subtractor D2, and the thus raised basis signal may be displayed via an indicating, displaying and/or recording arrangement A3 or may be subjected to further recalculations in calculator R to determine other desirable signals, such as osmotic pressure or osmolarity in accordance with equation (8) or (9), the results of which may be displayed in A4.

While the various above-described arrangements relate to measuring hydrogen ions, the actual measurement or indicia of ion strength for other ions may also be obtained according to the invention. Such measurements, of course, may pertain to ion indicators such as optical or electrochemical indicators.

While the present invention has been described in connection with what is presently considered to be the most practical and preferred embodiments, it is to be understood that the invention is not to be limited to the disclosed embodiments but on the contrary, is intended to cover various modifications, equivalent processes and equivalent arrangements included within the spirit and scope of the appended claims, which scope is to be accorded the broadest interpretation so as to encompass all such modifications, equivalent processes and equivalent arrangements.

What is claimed is:

1. Process for directly measuring the ion strength of an electrolyte solution comprising the combination of steps of:
    measuring the pH value of the electrolyte solution with a first indicator;
    measuring the pH of the electrolyte solution with a second indictator which is dependent on the ion strength in a manner different from said first indicator; and
    computing the ion strength J of said solution from said first pH measurement and said second pH measurement according to:

$$J = J_o \cdot 10^{F(N)} \left[ 1 + \frac{W(X) + 0.5}{W(N) - W(X)} \right] [pH'(N) - pH'(X)]$$

wherein
Jo = ion strength upon calibration;
pH'(N) = pH value, measured with the first indicator;
pH'(X) = pH value, measured with the second indicator;
W(N) = valency of the first indicator
W(X) = valency of the second indicator; and $$F(N) = -\frac{1}{0.07[2W(N) + 1]}.$$

2. Process as in claim 1, wherein said first and said second indicators are two different fluorescence indicators.

3. Process as in claim 2, wherein said first indicator is hydroxypryrenetrisulfonate and said second indicator is b-methylumbelliferon.

4. Process as in claim 2, wherein a reference indicator is added to said fluorescence indicators to eliminate intensity fluctuations.

5. Process as in claim 1, wherein said second indicator is a pH-electrode and wherein $$F(N)\left[ 1 + \frac{W(X) + 0.5}{W(N) - W(X)} \right]$$

is approximately 2.22, said first indicator being a fluorescence indicator hydroxypyrenetrisulfonate.

6. Process for the fluorescence photometric measurement of the pH value of an unknown solution of electrolytes, comprising the combination of steps of:
    measuring the pH of an unknown solution of electrolytes with a first fluorescence pH indicator X and generating a pH'(X) signal;
    measuring the pH of said solution with a second fluorescence pH indicator N, said second indicator being different from said first indicator and having an ion strength dependence different from said first indicator, and generating a pH'(N) signal; and
    computing the actual pH of said solution from pH'(X), the signal difference between pH'(X) and pH'(N), and the ion valency adjusted signal difference between said respective pH signals, said computing being governed by:

$$pH = pH'(X) - WF[pH'(N) - pH'(X)]$$

wherein
pH'(N) = apparent pH(N);
pH'(X) = apparent pH(X);
pH = actual pH;
WF = valency factor,
wherein said valency factor is computed in accordance with:

$$WF = \frac{W(X) + 0.5}{W(N) - W(X)} \text{ and}$$

wherein
W(X) = valency of indicator X; and
W(N) = valency of indicator N.

7. Apparatus for directly measuring the ion strength of an electrolyte solution comprising:
    means including a first indicator for measuring the pH value of an electrolyte solution,
    means including a second indicator for measuring the pH of the electrolyte solution,
    said second indicator being dependent on ion strength in a manner different from said first indicator, and
    means for determining ion strength J of said solution from said first pH measurement and said second pH measurement according to:

$$J = J_o \cdot 10^{F(N)} \left[ 1 + \frac{W(X) + 0.5}{W(N) - W(X)} \right] [pH'(N) - pH'(X)]$$

wherein
Jo = ion strength upon calibration;
pH'(N) = pH value, measured with the first indicator;
pH'(X) = pH value, measured with the second indicator;
W(N) = valency of the first indicator;
W(X) = valency of the second indicator; and $$F(N) = \frac{1}{0.07[2W(N) + 1]}$$

8. Apparatus as in claim 7, wherein said first and said second indicators are two different fluorescence indicators.

9. Apparatus as in claim 8, including a reference indicator combined to said fluorescence indicators to eliminate intensity fluctuations.

10. Apparatus as in claim 7, wherein said second indicator is a pH-electrode and wherein $$F(N)\left[1 + \frac{W(X) + 0.5}{W(N) - W(X)}\right]$$

is approximately 2.22, said first indicator being a fluorescence indicator.

11. Apparatus for directly measuring the ion strength of an electrolyte solution comprising:
   first and second means for determining the pH of an electrolyte solution and for respectively generating different first and second pH signals, said second pH determining means having an ion strength dependence different from said first pH determining means;
   subtracting means for receiving and operating on said first and second pH signals and for determining the signal difference between said pH signals;
   amplifying means for containing a basic signal $E_1$ based upon the product:

$$J_o \cdot 10^{F(N)}\left[1 + \frac{W(X) + 0.5}{W(N) - W(X)}\right]$$

wherein:
$J_o$ = ion strength upon calibration
$W(N)$ = valency of the first indicator
$W(X)$ = valency of the second indicator $$F(N) = \frac{1}{0.07\,[2W(N) + 1]}$$

and for raising said $E_1$ signal effectively by a power corresponding to said difference signal, and
   means for indicating said raised $E_1$ signal.

12. Apparatus as in claim 11 and further including means for calculating osmolarity of said electrolyte solution in accordance with:
   osmolarity = $2J$
   wherein $J$ = said raised $E_1$ signal.

13. Apparatus as in claim 11 and further including means for calculating osmotic pressure of said electrolyte solution in accordance with:
   osmotic pressure = $2|J| \times (22.4\,\text{Atm})$,
   wherein $J$ = said raised $E_1$ signal.

14. Apparatus for the fluorescence photometric measurement of the pH value of an unknown solution of electrolyes comprising:
   first fluroescence photometric means for measuring the pH of an electroylte solution and for generating a pH(N) signal;
   second fluorescence photometric means for measuring the pH of said electrolyte solution, said second pH measuring means having an ion strength dependence different from said first pH measuring means, and for generating a pH(X) signal;
   means operative on said pH(N) and pH(X) signals for determining the signal difference between said pH(N) and pH(X) signals, determining a valency adjusted signal difference from said pH(N) and pH(X) signals and generating a signal corresponding to the actual pH of said solution according to:

$$pH = pH'(X) - WF[pH'(N) - pH'(X)]$$

wherein
pH'(N) = apparent pH(N)
pH'(X) = apparent pH(X)
WF = valency factor;
wherein said valency factor is determined in accordance with $$WF = \frac{W(X) + 0.5}{W(N) - W(X)}$$

wherein
$W(X)$ = valency of said first means for measuring pH
$W(N)$ = valency of said second means for measuring pH
and means for indicating said actual pH signal.

15. Apparatus as in claim 14, wherein said apparatus further comprises:
   means for determining the ion strength of the electrolyte solution by raising to a power, which corresponds to said difference signal between pH(N) and pH(X), a product signal based on:

$$J_o \cdot 10^{2.22},$$

in which $J_o$ is the ion strength upon calibration, and generating a signal corresponding to the thus determined ion strength of the electrolyte solution.

16. Apparatus for directly measuring the ion strength of an electrolyte solution comprising:
   fluorescence photometric means for measuring the pH of an electrolyte solution and for generating a first pH signal;
   pH-electrode means for measuring the pH of the electrolyte solution and for generating a second pH signal;
   subtracting means responsive to said respective pH signals for computing the signal difference between said first and second pH signals and generating a difference signal;
   amplifying means responsive to said difference signal for raising a basis $E_2$ to a power corresponding to said difference signal wherein the basis is in accordance with:

$$E_2 = J_o \times 10^{2.22},$$

wherein $J_o$ is a calibrated ion strength; and
   means for indicating said raised $E_2$ signal.

17. Apparatus as in claim 16 further comprising second indicating means connected to said pH-electrode means for indicating said second pH signal.

18. Apparatus for the fluorescence photometric measurement of the pH value of an unknown solution of electrolytes, consisting essentially of:
   fluorescence photometric means including a first pH indicator X for measuring the pH of an unknown solution of electrolytes and generating a pH'(X) signal;
   fluorescence photometric means including a second pH indicator N for measuring the pH of said solution and generating a pH'(N) signal, said second pH indicator having an ion strength dependence different from said first pH indicator; and
   means for determining the actual pH of said solution from pH'(X), the signal difference between pH'(X) and pH'(N), and the ion valency adjusted signal difference between said respective pH signals, in accordance with:

actual $pH = pH'(X) - WF[pH'(N) - pH'(X)]$ wherein
pH'(N) = apparent pH(N);
pH'(X) = apparent pH(X);
WF = valency factor,
wherein said valency factor is determined in accordance with:

$$WF = \frac{W(X) + 0.5}{W(N) - W(X)}$$ and wherein
W(X) = valency of indicator X; and
W(N) = valency of indicator N.

* * * * *